United States Patent [19]

Semeraro et al.

[11] Patent Number: 5,162,345
[45] Date of Patent: Nov. 10, 1992

[54] HETEROCYCLIC COMPOUNDS AND THEIR PREPARATION AND PHARMACEUTICAL FORMULATION

[75] Inventors: Claudio Semeraro, Bresso; Dino Micheli, Modena; Daniele Pieraccioli; Giovanni Gaviraghi, both of Verona, all of Italy; Alan D. Borthwick, London, England

[73] Assignee: Glaxo, S.p.A., Verona, Italy

[21] Appl. No.: 673,510

[22] Filed: Aug. 20, 1990

Related U.S. Application Data

[63] Continuation of Ser. No. 271,399, Nov. 10, 1988, abandoned, which is a continuation of Ser. No. 898,229, Aug. 20, 1986, abandoned.

[30] Foreign Application Priority Data

Aug. 21, 1985 [IT] Italy .................................. 21958A 85
Feb. 20, 1986 [IT] Italy .................................. 19480A 86

[51] Int. Cl.$^5$ .................. C07D 211/86; A61K 31/455
[52] U.S. Cl. ..................................... 514/356; 546/321;
546/283; 546/194; 544/60; 544/124; 544/360;
514/343; 514/318; 514/218; 514/235.5;
514/227.8
[58] Field of Search ...................... 546/321; 514/356

[56] References Cited

U.S. PATENT DOCUMENTS

| | | | |
|---|---|---|---|
| 3,923,818 | 12/1975 | Bossert et al. | 546/321 |
| 4,307,103 | 12/1981 | Sato et al. | 546/321 |
| 4,430,333 | 2/1984 | Campbell et al. | 546/321 |
| 4,492,703 | 1/1985 | Goldmann et al. | 546/321 |
| 4,801,599 | 1/1989 | Semeraro et al. | 546/321 |
| 4,806,533 | 2/1989 | Semeraro et al. | 546/321 |

FOREIGN PATENT DOCUMENTS

0060674 9/1982 European Pat. Off. ............ 546/321
247345 12/1987 European Pat. Off. .
3607821 9/1987 Fed. Rep. of Germany .

OTHER PUBLICATIONS

Rahwan Annual Reports in Medicinal Chem. 16, 1981, p. 257.
Thomas, G. et al., J. Cardiovascular Pharm. 6, pp. 1170–1176 (1984).

Primary Examiner—Jane T. Fan
Attorney, Agent, or Firm—Morgan & Finnegan

[57] ABSTRACT

Compounds are described of the formula:

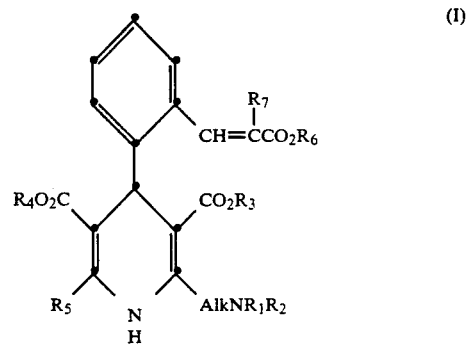

(I)

and physiologically acceptable salts thereof, in which $R_1$–$R_7$ are defined hereinafter.

The compounds represented by formula (I) reduce intracellular calcium ion concentration by limiting transmembranal calcium ion concentration and thus may be useful for the treatment of cardiovascular disorders such as hypertension.

19 Claims, No Drawings

HETEROCYCLIC COMPOUNDS AND THEIR PREPARATION AND PHARMACEUTICAL FORMULATION

This is a continuation of co-pending application Ser. No. 07/271,399, filed on Nov. 10, 1988 now abandoned. which is a continuation of co-pending application Ser. No. 06/898,229, filed on Aug. 20, 1986.

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. It has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heart failure, cerebral vascular and peripheral disorders. Such compounds may also be useful and for the treatment of diseases characterised by reversible airway obstruction such as asthma and chronic bronchitis.

The invention thus provides compounds of the general formula (I)

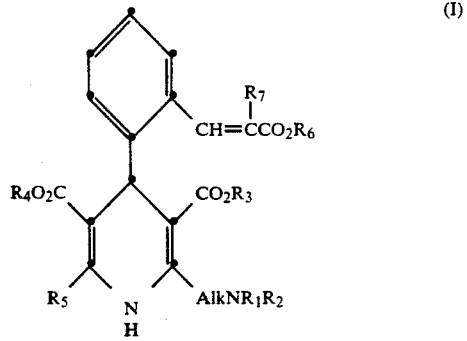

(I)

and physiologically acceptable salts thereof, in which
$R_1$ represents hydrogen or $C_{1-4}$ alkyl, $R_2$ represents hydrogen, $C_{1-6}$ alkyl or phenyl($C_{1-3}$)alkyl in which the phenyl ring may be substituted by a nitro, $C_{1-3}$ alkyl, $C_{1-3}$ alkoxy or hydroxyl group or a halogen atom, or $R_1$ and $R_2$ may together with the nitrogen atom to which they are attached form a pyrrolidino, piperidino, hexamethylenimino, morpholino, thiamorpholino, thiamorpholino S-oxide, thiamorpholino S,S-dioxide, piperazino, N-methylpiperazino or N-phenylpiperazino ring;
Alk represents a methylene or ethylene chain.
$R_3$ and $R_4$ independently represent a $C_{1-6}$ straight or branched chain alkyl or alkoxyalkyl group;
$R_5$ represents $C_{1-4}$ alkyl;
$R_6$ represents a $C_{1-13}$ alkyl group or a $C_{5-8}$ cycloalkyl group which may be substituted by $C_{1-3}$ alkyl; and
$R_7$ represents a halogen or hydrogen atom or a $C_{1-3}$ alkyl group.

The compounds represented by formula (I) can exist in more than one isomeric and/or enantiomeric form and the invention includes all such isomers, enantiomers and mixtures thereof.

The term 'alkyl' as a group means that the group is straight or branched.

The compounds of formula (I) form salts with inorganic and organic acids, and the invention includes such salts. Particularly useful salts are those of physiologically acceptable inorganic and organic acids and include hydrochlorides, hydrobromides, sulphates, tosylates, methanesulphonates, acetates, maleates, fumarates, formates, succinates, phosphates, citrates, benzoates, tartrates and dibenzoyl tartrates. The hydrochloride and hydrobromide salts are preferred.

When $R_1$ represents $C_{1-4}$ alkyl and/or $R_2$ represents $C_{1-6}$ alkyl they may independently be for example methyl, ethyl, propyl or isopropyl groups.

Examples of suitable groups for $R_3$ and $R_4$ independently include $C_{1-4}$ alkyl such as methyl, ethyl, isopropyl, isobutyl or tertiary butyl or $C_{1-3}$ alkyl (such as ethyl) substituted by $C_{1-3}$ alkoxy (e.g. methoxy or propoxy).

Examples of suitable groups for $R_5$ include methyl and ethyl groups.

When the group $R_6$ represents a $C_{1-13}$ alkyl group this may for example be a methyl, ethyl, propyl, isopropyl, butyl, isobutyl, tertiary butyl, pentyl, isopentyl, neopentyl, hexyl, 2,6-dimethyl-4-heptyl or octyl group. When $R_6$ represents a cycloalkyl group, conveniently this represents a cyclopentyl, cyclohexyl or a cycloheptyl group which may be substituted by a methyl group.

When the group $R_7$ represent a $C_{1-3}$ alkyl group this may for example be a methyl, ethyl or n-propyl group.

When the group $R_7$ represents halogen this may be for example chlorine, bromine or iodine.

The group $-CH=CR_7CO_2R_6$ in the compounds of formula (I) can exist in the cis or the trans configuration. Preferred compounds are those in which the hydrogen atom and the group $R_6$ are in the trans configuration with respect to each other and these isomers are referred to hereinafter as trans isomers.

The compounds of the invention have an asymmetric carbon atom at the 4-position in the dihydropyridine ring and formula I includes both enantiomers and mixtures thereof. The two individual enantiomers may be represented by formulae (Ia) and (Ib) and the enantiomer represented by formula (Ib) and hereinafter referred to as the S-enantiomer is preferred. The enantiomer represented by formula (Ia) is hereinafter referred to as the R-enantiomer.

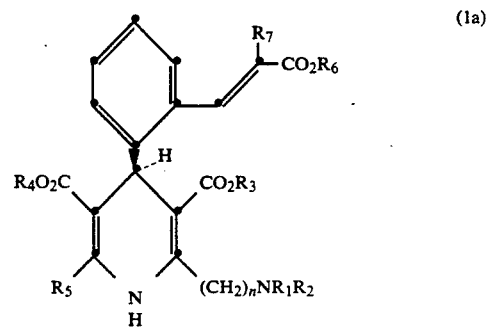

(Ia)

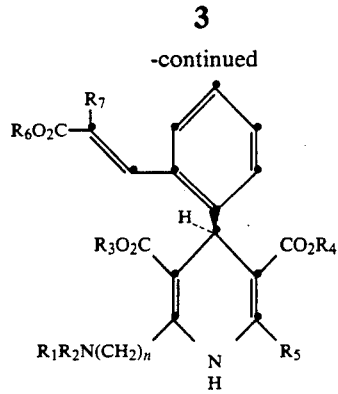

Preferred compounds of formula (a) are those in which $R_1$ preferably represents hydrogen or methyl and $R_2$ preferably represents hydrogen or a $C_{1-4}$ alkyl group such as methyl, ethyl, propyl or isopropyl.

When $R_1$ and $R_2$ together with the nitrogen atom to which they are attached form a heterocyclic ring this is preferably pyrrolidino, piperidino, morpholino, piperazino and thiomorpholino.

$R_3$ and $R_4$ preferably independently represent $C_{1-4}$ alkyl e.g. methyl or ethyl.

$R_5$ preferably represents methyl.

$R_6$ preferably represents a $C_{2-9}$ alkyl group such as an ethyl, propyl, isopropyl, tertiary butyl, pentyl or octyl group, or a $C_{5-7}$ cycloalkyl group which may be substituted by a $C_{1-3}$ alkyl group e.g. cyclohexyl; $R^7$ preferably represents a bromine or a hydrogen atom or a $C_{1-3}$ alkyl group such as a methyl or ethyl group.

A particularly preferred class of compounds of the invention are those of formula (I) wherein $R_1R_2N$ represents an amino, methylamino, ethylamino, isopropylamino, dimethylamino or morpholino group, Alk represents an ethylene or more particularly a methylene chain, $R_3$ and $R_4$ independently represent methyl or ethyl, more particularly ethyl, $R_5$ represents methyl, $R_6$ represents cyclohexyl or $C_{2-9}$ alkyl, for example ethyl propyl, isopropyl, tertiary butyl, pentyl or octyl, and $R_7$ represents a hydrogen atom or a methyl or ethyl group.

A further particularly preferred class of compounds of the invention are those of formula (I) wherein $R_1R_2N$ represents a methylamino, isopropylamino, dimethylamino or morpholino group, Alk represents a methylene chain, $R_3$ and $R_4$ independently represent an ethyl or methyl group, $R_5$ represents methyl and $R_6$ represents an isopropyl or more particularly a tert butyl group when $R_7$ represents a hydrogen or $R_6$ represents $C_{2-6}$ alkyl group, more particularly an ethyl, isopropyl, propyl, tert butyl or pentyl group and $R_7$ represents a methyl or ethyl group.

Particularly preferred compounds according to the invention are:

2-dimethylaminomethyl-6-methyl-4-(2-(3-(1,1-dimethylethoxy)-3-oxo-1-propenyl)phenyl-1,4-dihydropyridine-3,5-dicarboxylic acid diethyl ester; and more especially the trans (E) isomer and S-enantiomers thereof and their physiologically acceptable salts, especially the hydrobromide or hydrochloride salt.

Other preferred compounds according to the invention are 2-methylaminomethyl-6-methyl-4-(2-(3-(1,1-dimethylethoxy)-3-oxo-1-propenyl)phenyl)-1,4-dihydropyridine-3,5-dicarboxylic acid diethyl ester;

2-aminomethyl-6-methyl-4-(2-(3-(1,1-dimethylethoxy)-3-oxo-1-propenyl)phenyl)-1,4-dihydropyridine-3,5-dicarboxylic acid diethyl ester;

2-isopropylaminomethyl-6-methyl-4-(2-(3-(1,1-dimethylethoxy)-3-oxo-1-propenyl)phenyl)-1,4-dihydropyridine-3,5-dicarboxylic acid diethyl ester;

2-methylaminomethyl-6-methyl-4-(2-(3-ethoxy-3-oxo-2-methyl-1-propenyl)phenyl)-1,4-dihydropyridine-3,5-dicarboxylic acid diethyl ester;

2-methylaminomethyl-6-methyl-4-(2-(3-ethoxy-3-oxo-2-ethyl-1-propenyl)phenyl)-1,4-dihydropyridine-3,5-dicarboxylic acid diethyl ester;

2-propylaminomethyl-4-(2-(3-(1,1-dimethylethoxy)-3-oxo-1-propenyl)phenyl)-6-methyl-1,4-dihydro-pyridine-3,5-dicarboxylic acid diethyl ester;

2-methylaminomethyl-4-(2-(3-(1,1-dimethylethoxy)-3-oxo-1-propenyl)phenyl)-6-methyl-1,4-dihydropyridine-3,5-dicarboxylic acid methyl ester ethyl ester;

2-dimethylaminomethyl-6-methyl-4-(2-(3-propoxy-3-oxo-2-methyl-1-propeny)phenyl)-1,4-dihydropyridine-3,5-dicarboxylic acid diethyl ester;

2-methylaminomethyl-6-methyl-4-(2-(3-propoxy-3-oxo-2-methyl-1-propenyl)phenyl)-1,4-dihydropyrdine-3,5-dicarboxylic acid diethyl ester;

and more particularly the trans (E) isomers and S-enantiomers thereof, and their physiologically acceptable salts.

The ability of compounds of the invention to limit or inhibit the effect of calcium ions on the tone of vascular smooth muscle was determined using a depolarised rabbit ear artery prepared according to the method of Towart. R. et al Br. J. Pharmacol. 1982, 75, 1508.

The antihypertensive activity of compounds of the invention was demonstrated by intravenous and/or oral administration of the compound to male spontaneously hypertensive rats.

In these tests compounds of the invention have been found to have a particularly advantageous profile of activity including a relatively long duration of action.

The compounds of the invention are thus of interest in the treatment of hypertension and diseases characterised by reversible airways obstruction such as asthma and chronic bronchitis.

They are also potentially useful for the treatment of other cardiovascular disorders including angina pectoris, myocardial ischaemia, congestive heart failure, cerebral vascular and peripheral disorders.

The compounds of the invention may be formulated in a conventional manner for use with one or more pharmaceutical carriers or excipients.

Thus a further aspect of the invention includes pharmaceutical compositions the compounds of formula (I) and/or physiologically acceptable addition salts thereof formulated for oral, sub lingual, transdermal, parenteral or rectal administration, or for administration by inhalation or insufflation.

For oral administration the pharmaceutical composition may take the form of for example tablets, which may be film or sugar coated, capsules, powders, granules, solutions including syrups, or suspensions prepared by conventional means with acceptable excipients. For sub lingual administration the composition may take the form of tablets or lozenges formulated in the conventional manner.

For parenteral administration the compounds of formula (I) may be given as a bolus injection or by continuous infusion. The compositions may take such forms as suspensions, solutions or emulsions in oily or aqueous vehicles and may contain formulatory agents such as suspending, stabilising and/or dispersing agents. For administration by injection these may take the form of an unit dose presentation or as a multidose presentation preferably with an added preservative.

Alternatively for parenteral administration the active ingredient may be in powder form for reconstitution with a suitable vehicle.

The compounds of formula (I) may be formulated as ointments and creams for transdermal administration and as suppositories or retention enemas for rectal administration.

For administration by inhalation the compounds of formula (I) are formulated so that they may be inhaled in the form of a very fine aerosol/powder dispersion.

A proposed daily dosage of active compound of the invention for the treatment of man is in the range of 0.03 mg to 100 mg, which may conveniently be administered in one or more doses. The precise dose employed will depend on the age and condition of the patient as well as the route of administration.

For oral use the compounds of the invention are conveniently administered to the human patient at a dose in the range 0.3 to 40 mg per day. For parenteral use the compounds of the invention are conveniently administered at a dose in the range of 0.01 to 2 mg, more preferably 0.03–1 mg per day.

For administration by inhalation use the compounds of the invention are conveniently administered to the human patient at a dose in the range of 0.1 mg to 10 mg per day.

For oral use the compound is preferably administered twice or more particularly once a day.

Methods for preparing the compounds of formula (I) are described below and for the intermediates described below $R_1$–$R_7$ and Alk have the meanings defined above for compounds of formula (I) or are such groupings in a protected form unless otherwise stated.

Compounds of formula (I) in which Alk represents methylene may be prepared from compounds of formula (II), in which X is a leaving group such as halogen

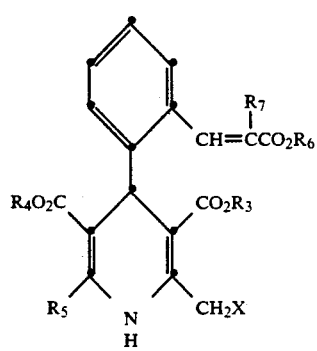
(II)

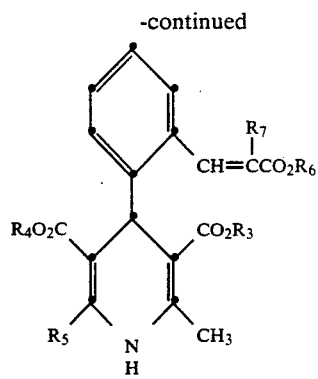
(III)

and the appropriate amine $R_1R_2NH$. The reaction is preferably carried out in an aprotic solvent such as a halohydrocarbon e.g. chloroform, dichloromethane or 1,1,1-trichloroethane and at a temperature in the range $-20°$ to $+20°$ C., more preferably below 0° C. The reaction may also conveniently be carried out in the presence of an additional base, for example pyridine.

The compounds of formula (II) are conveniently prepared in situ from the compounds of formula (III).

Thus the compound of formula (III) may be treated with a suitable halogenating agent such as chlorine, bromine, N-chlorosuccinimides or N-bromosuccinimide or more particularly, pyridine-hydrobromide-perbromide. The halogenation reaction may conveniently be carried out in a suitable aportic solvent such as chloroform, or more conveniently, dichloromethane at a temperature within the range of $-20°$ to 40° C., preferably $-15°$ to 20° C. Compounds of formula (II) wherein X represents iodine may be prepared by ion exchange from the corresponding bromide.

The trans isomers of compounds of formula (I) in which $R_1$ and/or $R_2$ are not hydrogen and $R_7$ is hydrogen or an alkyl group, may also be prepared from compounds of formula (IV)

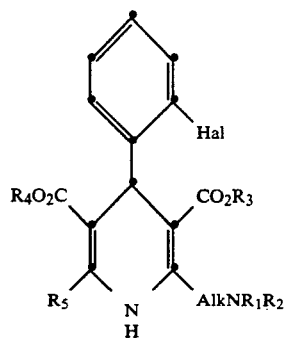
(IV)

(where Hal represents bromine or iodine) by reaction with an acrylic ester

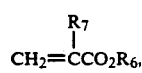

in which $R_7$ is hydrogen or an alkyl group.

The reaction takes place in the presence of a catalytic amount of palladium salt such as palladium acetate in the presence of a suitable organic base such as a trialkylamine e.g. triethylamine or tri-n-butylamine. The reaction is also preferably carried out in the presence of a triaryphosphine such as tri-o-tolylphosphine or triphenylphosphine.

The reaction is conveniently carried out in a suitable solvent such as xylene or t-butyl acetate, or more conveniently in dimethylacetamide, dimethylformamide or in a mixture of solvents e.g. xylene/dimethylformamide, preferably with heating. The reaction mixture is preferably heated within the temperature range of 60° to 150° C., more preferably at 80° to 110° C.

Alternatively, the compounds of formula (I) in which Alk represents ethylene may be prepared from compounds of formula (III) by aminomethylation involving reaction with an amine $R_1R_2NH$ or a salt thereof and formaldehyde. The reaction may be carried out by reacting an aqueous solution of the amine with aqueous formaldehyde and the compound (III) in the presence of a suitable acid such as glacial acetic acid with heating, preferably within the range of 80° to 100° C. Alternatively when the amine is used in the form of its hydrochloride salt the reaction may be carried out using an alkanol such as ethanol as solvent in the presence of hydrochloric acid under reflux.

In a further process of the invention compounds of formula (I) may be prepared by esterifying the corresponding acid of formula (I) in which $R_6$ is hydrogen. Thus in one embodiment of this process compounds of formula (I) may be prepared by treating a compound of formula (I) in which $R_6$ is hydrogen with an alkylating agent $R_6X$ where $R_6$ is as defined in formula (I), and X is a leaving group such as halogen or mesylate. The reaction is preferably carried out in the presence of a base such as an alkali or alkaline earth metal carbonate e.g. potassium carbonate in a polar aprotic solvent such as dimethylformamide or dimethylsulphoxide optionally with heating. Thus for example the reaction may be carried out a temperature within the range 10°-100° C.

In a further embodiment of this process compounds of the invention may be prepared from the corresponding carboxylic acid of formula (I) in which $R_6$ is hydrogen, via an activated derivative thereof such as a mixed anhydride, by reaction with an appropriate alcohol $R_6OH$, where $R_6$ is as defined in formula (I), or the corresponding alkoxide thereof.

The compounds of formula (I) wherein $R_6$ represents hydrogen may be prepared by hydrolysis of a compound of formula (I) wherein $R_6$ represents a tertiary butyl group. The hydrolysis may be carried out using hydrogen bromide in acetic acid, in the presence of a solvent such as dichloromethane. Preferably the reaction is carried out at low temperatures e.g. $-78°-35°$ C.

The carboxylic acids represented by the compounds of formula (I) wherein $R_6$ represents hydrogen are new compounds and useful chemical intermediates for preparing the compounds of formula (I) and represent a further feature of the invention.

Compounds of formula (I) in which the group $-CH=CR_7CO_2R_6$ is in the cis configuration may be prepared by irradiating a solution of the corresponding trans isomer. Thus when a solution of the trans isomer in dichloromethane under a atmosphere of nitrogen is exposed to daylight a mixture of the cis and trans isomers are obtained and these may be separated by standard techniques such as fractional crystallisation and/or chromatography.

Compounds of formula (I) may also be prepared from the reaction of the compound (VI) with the phosphorane $Ph_3P=CR_7CO_2R_6$ in a suitable solvent such as dichloromethane, tetrahydrofuran or toluene. Preferably the reaction is carried out with heating for example 40°-120° C., conveniently at reflux.

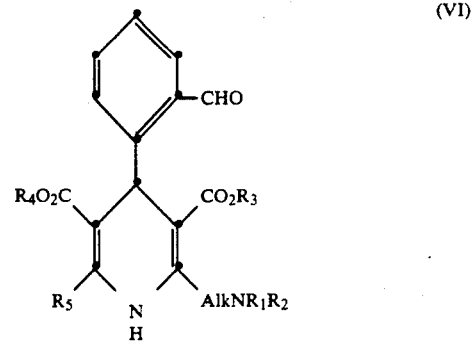

(VI)

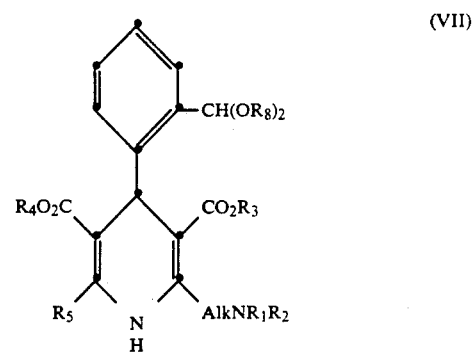

(VII)

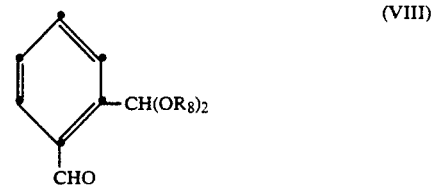

(VIII)

The intermediate (VI) may be prepared by aqueous acid hydrolysis of the corresponding acetal (VII); in which $R_8$ represents an alkyl group).

The compound of formula (VII) may be prepared from the aldehyde (VIII) by reaction with a compound of formula (XI) and/or (XIII) under the conditions described below for preparing compounds of formula (III) from the intermediate (XI). The intermediate (VIII) may be prepared from the bromobenzene derivative (IX) by reaction with butyl lithium in solvent followed by addition of dimethylformamide.

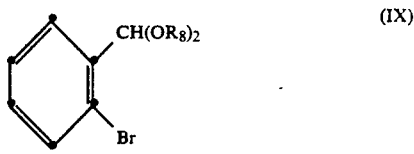

(IX)

Compounds of formula (III) may be prepared by reacting the $\alpha,\beta$-unsaturated ketone (IX) with the aminoester (X). The reaction is conveniently carried out in a solvent such as an alkanol, e.g. ethanol or isopropanol and preferably with heating e.g. 40°-150° C.

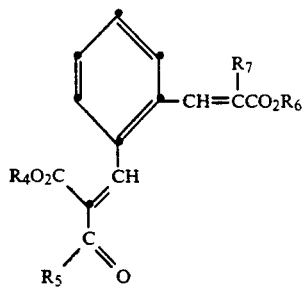 (X)

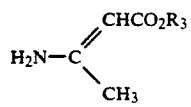 (XI)

The α,β-unsaturated ketone (X) may be prepared by reacting the aldehyde (XII) with the ketoester (XIII), in a solvent such as an alkanol e.g. ethanol or isopropanol, preferably with heating. Conveniently this reaction is carried out in the presence of a catalyst such as piperidine acetate.

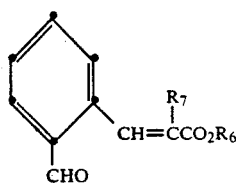 (XII)

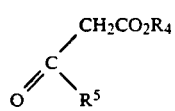 (XIII)

In a modification of this process the aldehyde (XI) may be reacted with a mixture of the aminoester (XI) and the ketoester (XIII) under the conditions previously described for the reaction of the α,β-unsaturated ketone (X) with the aminoester (XI).

Compounds of formula (III) in which $R_3$ and $R_4$ are the same and $R_5$ is a methyl group may be prepared by reacting the aldehyde (XII) with the aminoester (XI) in the presence of a suitable acid catalyst. Examples of suitable acid catalysts include organic acids such as oxalic acid, alkanoic acids e.g. acetic acid or haloalkanoic acids such as trichloroacetic acid or trifluoroacetic acid or pyridinium salts thereof, or a sulphonic acid such as an alkanesulphonic acid e.g. methanesulphonic acid or an aryl sulphonic acid e.g. benzenesulphonic acid or p-toluenesulphonic acid or a tetrahaloboric acid such as tetrafluoroboric acid. The reaction may be carried out in the presence of a solvent and preferably at a temperature within the range of −70° to 30° C. more preferably at −30° to 20° C. Suitable solvents for the reaction include aprotic solvents such as hydrocarbons, e.g. hexane or cyclohexane, acetonitrile or ethers such as tertiary butyl methyl ether, dioxan or tetrahydrofuran, or protic solvents such as an alkanol e.g. methanol, ethanol, propanol, isopropanol or butanol.

Compounds of formula (XII) in which $R_7$ has the meanings given other than a halogen atom may be prepared by reacting a 2-halobenzaldehyde (XIV)

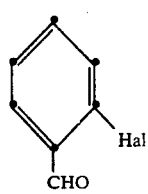 (XIV)

(where Hal represents bromine or iodine) with an acrylic ester

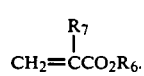

under the conditions described for the reaction between the compounds of formula (IV) with the acrylic ester $$CH_2=CR_7CO_2R_6.$$

The compounds of formula (XII) may also be prepared by reacting the bis aldehyde (XV) with the triphenylphosphorane $Ph_3P=CR_7CO_2R_6$ in a solvent such as chloromethane, dichloromethane or toluene.

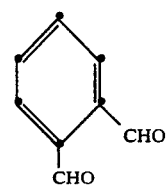 (XV)

The compounds of formula (IV) may be prepared from compounds of formula (XVI)

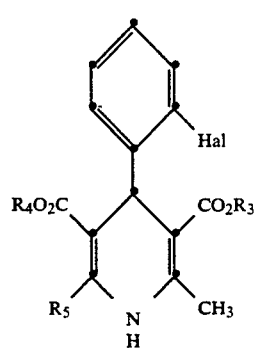 (XVI)

using amination and aminomethylation procedures previously described for the preparation of compounds of formula (I).

Compounds of formula (I) may also be prepared by the reaction of the α,β unsaturated ketone (X) with the diaminoester (XVII). The reaction is conveniently carried out in a solvent such as an alkanol e.g. ethanol or isopropanol and preferably with heating e.g. 40°–150° C.

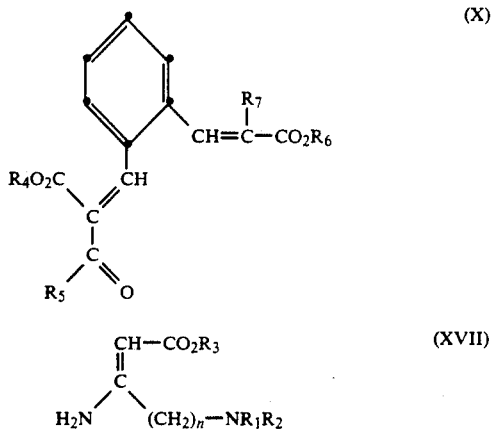

(XVII)

CH—CO₂R₃
||
C
/ \
H₂N   (CH₂)$_n$—NR₁R₂

For the preparation of compounds of formula I in which R₁ and/or R₂ represent a hydrogen atom then it is necessary to use a diaminoester of formula (XVII) in which R₁ and R₂ represent a group that may be removed to give a hydrogen atom. Thus compounds of formula I in which R₁ and R₂ both represent hydrogen may be prepared by using a diaminoester (XVII) wherein the group NR₁R₂ is a phthalimido group. The resultant compound of formula I wherein R₁R₂N represents a phthalamido group may then be converted into the compound wherein R₁ and R₂ represent hydrogen by treatment with hydrazine in a suitable solvent such as an alkanol.

The intermediates of formula (XVI) may be prepared from compounds of formulae (XI), (XIII) and (XIV) in an analogous reaction to that previously described for the preparation of the compounds of formula (III) from compounds of formulae (XI), (XII) and (XIII).

Compounds of formula I wherein one of the groups R₁ or R₂ represent hydrogen may be prepared by treating the corresponding compound of formula I in which the appropriate group R₁ or R₂ is a benzyl group, with a suitable ester of chloroformic acid, and subsequent hydrolysis of the resultant carbamate derivative. Suitable esters of chloroformic acid include haloethyl chloroformates, such as trichloroethylformate and conveniently this stage of the reaction is carried out in a solvent such as a hydrocarbon, for example toluene and preferably with heating. The hydrolysis of the resultant carbamate e.g. trichloroethylcarbamate may be carried out using zinc and an appropriate acid such as formic or acetic acid, and optionally in a solvent such as dimethylformamide.

In the general processes described above for the preparation of compounds of formula I, the required product may be obtained and/or isolated in the form of a salt, conveniently in the form of a physiologically acceptable salt. Where desired such salts may be converted into the corresponding free base of formula I using conventional methods.

Physiologically acceptable salts of the compounds of formula (I) may be prepared by reacting a compound of general formula I with an appropriate acid in a suitable solvent such as acetone, ethyl acetate or an alkanol e.g. ethanol.

When a specific enantiomer of formula (1a) or (1b) or required, this may be obtained by resolution of a mixture of enantiomers of the corresponding compound of general formula (1) using conventional methods. Thus in one example an appropriate optically active acid may be used to form salts with a mixture of enantiomers of a compound of general formula I. The resulting mixture of isomeric salts may be separated, for example by fractional crystallisation into the individual diastereoisomeric salts from which the required enantiomer of formula (1a) or (1b) may be isolated as either the free base or another salt thereof.

The compounds of formulae (V), (IX), (XI), (XIII), (XIV), (XIV) and (XVII) are either known compounds or may be made by analogous processes to those used for known compounds.

The following examples illustrate the invention. Temperatures are in °C. Throughout the examples reference to t.l.c. means thin layer chromatography on silica plates and, unless otherwise stated, using ethyl acetate/cyclohexane/methanol (7:3:2) as solvent. Column chromatography was carried out on silica gel eluting with ethyl acetate/cyclohexane/methanol (7:3:2) unless otherwise stated.

INTERMEDIATE 1

4-(2-Bromophenyl)-1,4-dihydro-2,6-dimethyl-3,5-pyridinecarboxylic acid, diethyl ester

INTERMEDIATE 2

(E)-3-(2-Formylphenyl)-2-propenoic acid, 1,1-dimethyl ethyl ester

INTERMEDIATE 3

(E)-4-(2-(3-(1,1-Dimethylethoxy)-3-oxo-1-propenyl)-phenyl)-1,4-dihydro-2,6-dimethyl-3,5-pyridinedicarboxylic acid, diethyl ester

INTERMEDIATE 4

(a) (E)-3-(2-Formylphenyl)-2-methyl-2-propenoic acid ethyl ester

A solution of 2-(triphenylphosphoranilidene)-propanoic acid ethyl ester (8 g) in dry dichloromethane was added to a solution of ortho phthalaldehyde (2.9 g) in dry dichloromethane (10 ml) at 0° C. The solvent was evaporated and the oil taken up with diethyl ether. The solid triphenylphosphine oxide was filtered, washed with ether and the solution evaporated to dryness to give a colourless oil which was eluted on a silica gel column (diethyl ether/petrol ether, 1:1) to give the title compound as a colourless oil (4.3 g).

Similarly prepared was:

(b) (E)-3-(2-Formylphenyl)-2-methyl-2-propenoic acid 1,1-dimethylethyl ester

From 2-(triphenylphosphoranylidene)propanoic acid 1,1-dimethylethyl ester and ortho phthalaldehyde (c) (E)-3-(2-Formylphenyl)-2-ethyl-2-propenoic acid ethyl ester A solution of 2-(triphenylphosphoranilydene)-butanoic acid ethyl ester (5.6 g) in dry dichloromethane (10 ml) was added to a solution of ortho phthalaldehyde (2 g) in dry dichloromethane (10 ml) at 0° C. The solvent was evaporated and the oil taken up with diethyl ether. The solid triphenylphosphine oxide was filtered, washed with ether and the solution evaporated to dryness to give a colourless oil which was eluted on a silica gel column (gradient Petrol ether/ethyl acetate, 9:1–8:2) to give the title compound as a colourless oil (3 g).

Similarly prepared were:

(d) (E)-3-(2-Formylphenyl)-2-propyl 2-propenoic acid ethyl ester as a colourless oil From o-phthalaldehyde and 2-(triphenylphosphoranylidene)-pentanoic acid ethyl ester.

(e) (E)-3-(2-Formylphenyl)-2-ethyl-2-propenoic acid 1,1-dimethylethyl ester

From o-phthalaldehyde and 2-(triphenylphosphoranylidene)-butanoic acid 1,1-dimethylethyl ester.

INTERMEDIATE 5

(a)

(E)-4-(2-(3-Ethoxy-3-oxo-2-methyl-1-propenyl)phenyl-1,4-dihydro-2,6-dimethyl-3,5-pyridinedicarboxylic acid diethyl ester 3-Amino-2-butenoic acid ethyl ester was dissolved in acetic acid (3 ml) and treated with a solution of Intermediate 4(a) (3 g) in acetic acid (5 ml) at room temperature. The solution was stirred at room temperature for 2 h then poured into water and extracted with ethyl acetate. The organic phase was washed with 5% NaHCO$_3$ then with water and dried over Na$_2$SO$_4$. Evaporation of the solvent gave a yellow oil which was eluted twice on a silica gel column (Petrol ether/ethyl acetate, 7:3) to give a yellow solid. This was recrystallized from petrol ether/diethyl ether (1:1) to give the title compound as a pale yellow solid (0.45 g). M.p. 105°–106°.

Similarly prepared was:

(b)

(E)-4-(2-(3-(1,1-Dimethylethoxy)-3-oxo-2-methyl-1-propenyl)phenyl)-1,4-dihydro-2,6-dimethyl-3,5-pyridinedicarboxylic acid diethyl ester M.p. 130°–131°

From Intermediate 4(b) and 3-amino-2-butenoic acid ethyl ester.

(c)

(E)-4-(2-(3-Ethoxy-3-oxo-2-ethyl-1-propenyl)phenyl)-1,4-dihydro-2,6-dimethyl-3,5-pyridinedicarboxylic acid diethyl ester A solution of Intermediate 4(c) (6 g) in ethanol (50 ml) was cooled to −10° C. and then trifluoroacetic acid (4 ml) was added followed by a solution of 3-amino-2-butenoic acid ethyl ester (17 g) in ethanol (50 ml). The mixture was stirred at −10° C. for 1 hr, evaporated in vacuo and the residue taken up in ethyl acetate, washed with 10% HCl (3×50 ml), then with water and dried over Na$_2$SO$_4$. Evaporation of the solvent gave an oil which was purified by column chromatography on silica (Petrol ether/diethyl ether, gradient 7:3–3:7) to give the title compound as a white solid. M.p. 92°–94°.

Similarly prepared were:

(d)

(E)-4-(2-(3-Ethoxy-3-oxo-2-propyl-1-propenyl)phenyl)-1,4-dihydro-2,6-dimethyl-3,5-pyridinedicarboxylic acid diethyl ester M.p. 93°–95°

From Intermediate (4d) and 3-amino-2-butenoic acid ethyl ester.

(e)

(E)-4-(2-(3-(1,1-dimethylethoxy)-3-oxo-2-ethyl-1-propyl)phenyl)-1,4-dihydro-2,6-dimethyl-3,5-pyridine dicarboxylic acid diethyl ester M.p. 99°–101° C.

From Intermediate 4(e) and 3-amino-2-butenoic acid ethyl ester.

INTERMEDIATE 6

(a)

(E)-4-(2-(2-Carboxyl-1-propenyl)phenyl)-1,4-dihydro-2,6-dimethyl-3,5-pyridinedicarboxylic acid diethyl ester To a solution of Intermediate 5b (5 g) in dichloromethane (30 ml) at −78° was added a solution of 33% acetic acid/HBr (15 ml) in dichloromethane (30 ml) slowly. The mixture was then warmed to −30° and stirred at −30° C. for 20 minutes. The mixture was poured into ice water, NaHCO$_3$ (5 g) was added and the mixture was extracted with dichloromethane, washed with water and dried over Na$_2$SO$_4$. Evaporation of the solvent gave a solid which was recrystallized from petrol ether/ethyl acetate (1:1) to give the title compound as a white solid (3.5 g). M.p. 205°–207°.

(b) In a similar manner (E)-4-(2-(2-carboxy-1-butenyl)-phenyl)-1,4-dihydro-2,6-dimethyl-3,5-pyridinedicarboxylic acid diethyl ester was prepared from Intermediate 5(e).

INTERMEDIATE 7

(a)

(E)-4-(2-(3-Propoxy-3-oxo-2-methyl-1-propenyl)-phenyl-1,4-dihydro-2,6-dimethyl-3,5-pyridinedicarboxylic acid diethyl ester A suspension of Intermediate 6(a), propyl bromide and potassium carbonate in dimethylformamide was stirred at room temperature for 6 h. The mixture was poured into water and extracted with ethyl acetate, then washed thoroughly with water and dried over Na$_2$SO$_4$. Evaporation of the solvent gave an oil which was triturated with petrol and recrystallized from petrol ether to give the title compound. M.p. 108°–110°.

(b)

(E)-4-(2-(3-pentyloxy-3-oxo-2-methyl-1-propenyl)-phenyl)-1,4-dihydro-2,6-dimethyl-3,5-pyridinecarboxylic acid diethyl ester M.p. 126°–127° was prepared from Intermediate 6(a) and 1-bromopentane.

(c)

(E)-4-(2-(3-propoxy-3-oxo-2-ethyl-1-propenyl)phenyl)-1,4-dihydro-2,6-dimethyl-3,5-pyridinedicarboxylic acid diethyl ester was prepared from Intermediate 6(b) and propyl bromide.

(d)

(E)-4-(2-(3-pentyloxy-3-oxo-2-ethyl-1-propenyl)-phenyl)-1,4-dihydro-2,6-dimethyl-3,5-pyridinedicarboxylic acid diethyl ester was prepared from Intermediate 6(b) and 1-bromopentane.

INTERMEDIATE 8

4-(2-Formylphenyl)-1,4-dihydro-2-dimethylaminomethyl-6-methyl-3,5-pyridinedicarboxylic acid diethylester Pyridine hydrobromide perbromide (3.2 g) was added to a solution of 4-(2-formylphenyl)-1,4-dihydro-2,6-dimethyl-3,5-pyridinedicarboxylic acid diethylester (3.15 g) and pyridine (1.3 ml) in dicloromethane (100 ml) at 0° C. and stirred for 0.5 hours. The mixture was then cooled to −10° C., treated with dimethylamine (10.6 ml) and stirred at −10° C. for 1 hour. The solvent was evaporated and the residue taken up with ethyl acetate. The solid was filtered off and the solution evaporated to dryness to obtain a red oil, which was eluted on a silica gel column (Ethyl acetate/Petrol ether/Methanol, 7:3:1) to yield the title compound as a yellow solid (from petrol ether) (2.3 g), m.p. 115°–120° C. T.l.c. (CH$_2$Cl$_2$/Methanol, 95:5) Rf. 0.38.

INTERMEDIATE 9

2-Dimethylaminomethyl-6-methyl-(E)-4(-2(2-carboxyethenyl)phenyl)-1,4-dihydro-3,5-pyridinedicarboxylic acid diethylester, hydrobromide (1)

Method (A)

Pyridine hydrobromide perbromide was added to a solution of (E)-4(-2(2-carboxyethenyl)phenyl)-1,4-dihydro-2,6-dimethyl-3,5-pyridinedicarboxylic acid diethyl ester (3.5 g) and pyridine (2 ml) in dichloromethane (100 ml) at 0° C. and stirred at the same temperature for 30 mins. The mixture was then cooled to −10° C. and dimethylamine (10.6 ml) was slowly added. The mixture was stirred at −10° C. for 1 hour. The solvent was then evaporated and the residue taken up with methanol to yield the title compound as a yellow solid, which was recrystallised from petrol ether/methanol (8:2) (2.7 g), m.p. 145°–150° C. (dec). T.l.c. (CH$_2$Cl$_2$/Methanol, 8:2) Rf.=0.50

Method (B)

To a solution of the compound of Example 3 (1 g) in dichloromethane (10 ml), at −70° C. was added slowly a solution of 33% hydrogen bromide in acetic acid (3 ml) in dichloromethane (5 ml). The reaction was then warmed at −35° C. and after 10 minutes poured into ice/water. The pH was adjusted to 6 and the mixture extracted with dicloromethane washed with water and dried with CaCl$_2$. Evaporation of the solvent gave the free base of the title compound as a yellow solid (0.5 g), m.p. 135°–145° C. (dec.).

T.l.c. (CH$_2$Cl$_2$/Methanol, 8:2) Rf. 0.50.

INTERMEDIATE 10

(a) 3-Amino-4-dimethylamino-2-butenoic acid ethyl ester

Pyridine-hydrobromide-perbromide (48 g) was added to a solution of ethyl acetoacetate (19.4 g) in anhydrous methylene chloride (500 ml) at room temperature in 20 minutes. The mixture was stirred for 2 hours and then added dropwise to a solution of dimethylamine (48.8 g) in anhydrous methylene chloride (100 ml) at −15°–0° in 1 hr. The resulting mixture was cooled to −20° and ammonia was bubbled through the mixture under stirring for 1 hr and for 2 hr at room temperature. The reaction went to completion, by leaving the mixture overnight at about 5° C. After evaporation of the solvent the residue was treated with ether the solid was filtered off and the solution evaporated, to yield a brown oil, which was purified by column chromatography on silica gel to give the title compound (10.8 g) as an orange oil.

T.l.c. Rf.=0.4.

In a similar manner (b) 3-Amino-4-dimethylamino-2-butenoic acid methyl ester was obtained as a red oil. (T.l.c. Rf=0.38) from methyl acetoacetate (16.2 ml) and dimethylamine (60 ml).

INTERMEDIATE 11

3-(2-Formylphenyl)-2-bromo-2-propenoic acid, ethyl ester

A solution of 2-bromo-2-(triphenylphosphoranylidene)acetic acid, ethyl ester (15 g) in dry dichloromethane (30 ml) was added to a solution of orthophthaldehyde (4.7 g) in dry dichloromethane (30 ml), at 0° C. The solvent was evaporated and the oil taken up with diethyl ether. The solid triphenylphosphine oxide was filtered, washed with ether and the solution evaporated to dryness to give a colourless oil which was eluted on a silica gel column (gradient petrol ether/ethyl acetate, 8:2→6:4) to give the title compound (6.2 g) as a colourless oil (6.2 g). T.l.c. (Petrol ether/ethyl acetate, 7:3) Rf.=0.41.

INTERMEDIATE 12

(Z)-4-(2-(3-Ethoxy-3-oxo-2-bromo-1-propenyl)phenyl)-1,4-dihydro-2,6-dimethyl-3,5-pyridinedicarboxylic acid, diethyl ester A solution of Intermediate 11 (5.5 g) in ethanol (50 ml) was cooled to −10° and then trifluoracetic acid (4 ml) was added followed by a solution of 3-amino-2-butenoic acid, ethyl ester (12.3 g) in ethanol (50 ml). The mixture was stirred at −10° for 1 h, evaporated in vacuo and the residue taken up in ethyl acetate, washed with 10% HCl, then with water and dried over Na$_2$SO$_4$. Evaporation of the solvent gave an oil. Purification of the oil by column chromatography (gradient diethyl ether/petrol ether, 8:2→9:1) gave the title compound as a white solid (3.2 g). M.p. 137°. T.l.c. (petrol ether/ethyl acetate, 1:1) Rf=0.38.

INTERMEDIATE 13

(a) 2-(2-(3-(1,1-Dimethylethoxy)-3-oxo-1-propenyl) phenyl)-methylene-3-oxo-butanoic acid, methyl ester A solution of piperidine (0.11 g) and acetic acid (0.078 g) in isopropanol (1 ml) was added to a solution of Intermediate 2 (5.2 g) and methyl acetoacetate (2.55 g) in isopropanol (15 ml). The mixture was stirred at 60° C. for 1h, then the solvent was evaporated and the residue taken up with ether (100 ml). The solution was washed with 1N HCl, water, with saturated bicarbonate solution, then water again and dried over Na$_2$SO$_4$. Evaporation of the solvent gave an oil which was purified by column chromatography (gradient Petrol/Ether, 7:3-1:1) to give the title compound as a pale oil (4.2 g; mixture E/Z isomers).

The following compounds were prepared in a similar manner.

(b) 2-(2-(3-(1,1-Dimethylethoxy)-3-oxo-1-propenyl)-phenyl)-methylene-3-oxo-butanoic acid ethyl ester was prepared from Intermediate 2 and ethyl acetoacetate.

(c) 2-(2-(3-Ethoxy-3-oxo-2-ethyl-1-propenyl)phenyl) methylene-3-oxo-butanoic acid methyl ester from Intermediate 4(c) and methyl acetoacetate.

EXAMPLE 1

2-Aminomethyl-6-methyl-4(E)(2-(3-(1-1-dimethylethoxy)-3-oxo-1-propenyl)phenyl)-1,4-dihydro-3,5-pyridine dicarboxylic acid diethyl ester hydrobromide Pyridine-hydrobromide-perbromide (13.5 g) was added to a solution of Intermediate 3 (15.4 g) and pyridine (5ml) in anhydrous methylene chloride (350 ml) at 0° in 10 minutes. The mixture was stirred at 0°-3° for 30 minutes and then dropped into a saturated solution of ammonia in methylene chloride (180 ml) at −10° in 30 minutes. Ammonia was bubbled through the resulting mixture under stirring for 1.30 h, at −10° to −5° and then for 2 hours at room temperature. The solid pyridine hydrobromide was filtered off and the solution washed with 0.1N HBr and brine. After evaporation of the solvent the residue was purified by column chromatography to give the title compound (4.2 g). M.p. 165°-8°. T.l.c. Rf 0.2.

EXAMPLE 2

2a
2-Isopropylaminomethyl-6-methyl-4(E)(2-(3-(1,1-dimethyl-ethoxy)-3-oxo-1-propenyl)phenyl)-1,4-dihydro-3,5-pyridine-dicarboxylic acid diethyl ester hydrobromide Pyridine-hydrobromide-perbromide (4.5 g) was added to a solution of Intermediate 3 (5.1 g) and pyridine (1.75 ml) in anhydrous methylene chloride (125 ml) at 0° C. in 10 minutes. The mixture was stirred at 0°-3° for 30 minutes and then dropped into a solution of isopropylamine (6.5 ml) in methylene chloride (50 ml) at 0° in 20 minutes. The resulting mixture was stirred for 2 h at room temperature. The solid was filtered off and the solution washed with 0.1N HBr and brine. After evaporation of the solvent the residue was treated with ethyl acetate/ethyl ether to give a yellow precipitate of the title compound (3.1 g). M.p. 218°-220°. T.l.c. Rf 0.28.

The free base of the title compound m.p. 135°-137° was obtained by treatment of the hydrobromide with inorganic base.

Microanalysis for $C_{29}N_{40}N_2O_6$ Requires C67.94; H7.86; N5.46; Found C68.21; H7.84; 5.49%

Treatment of the free base with equimolar amount of hydrochloric acid gave the corresponding hydrochloride M.p. 204°-205°.

Similarly were prepared:-

2b
2-Methylaminomethyl-6-methyl-4(E)(2-(3-(1,1-dimethylethoxy)-3-oxo-1-propenyl)phenyl)-1,4-dihydro-3,5-pyridine-dicarboxylic acid diethyl ester hydrobromide (5.5 g)

m.p. 208°-210°. T.l.c. Rf 0.125 from Intermediate 3 (10.2 g) and methylamine (10 ml).

The free base of the title compound was obtained by treating the hydrobromide with a solution of sodium hydroxide. M.p. 151°-153°.

2c
2-Dimethylaminomethyl-6-methyl-4(E)(2-(3-(1,1-dimethylethoxy)-3-oxo-1-propenyl)phenyl)-1,4-dihydro-3,5-pyridine-dicarboxylic acid diethyl ester hydrobromide (1.6 g) M.p. 192°-194°. T.l.c. Rf 0.33 from Intermediate 3 (5.1 g) and dimethylamine (5 ml).

2d
2-Methylaminomethyl-6-methyl-4(E)-(2-(3-ethoxy-3-oxo-2-methyl-1-propenyl)phenyl)-1,4-dihydro-3,5-pyridinedicarboxylic acid diethyl ester (3 g). M.p. 96°-98°. T.l.c. (ethyl acetate/methanol, 1:1) Rf 0.22 from Intermediate 5a (5.08 g) and methylamine (7 ml).

The corresponding hydrobromide salt was obtained by treating a solution of the free base (940 mg) in methanol/acetone (3:1) with 0.1N HBr (20 ml). The mixture was dried in vacuo and treated with diethyl ether to give the hydrobromide (850 mg). M.p. 245°-247°. The corresponding hydrochloride salt was also obtained. M.p. 230°-232°.

2e
2-Isopropylaminomethyl-6-methyl-4(E)-(2-(3-ethoxy-3-oxo-2-methyl-1-propenyl)phenyl)-1,4-dihydro-3,5-pyridinedicarboxylic acid diethyl ester (850 ml) from Intermediate 5a (3.15 g) and isopropylamine (4.82 ml).

The corresponding hydrochloride salt was obtained. M.p. 124°-128°.

2f
2-Dimethylaminomethyl-6-methyl-4(E)-(2-(3-ethoxy-3-oxo-2-methyl-1-propenyl)phenyl)-1,4-dihydro-3,5-pyridinedicarboxylic acid diethyl ester (1.15 g) from Intermediate 5a (2.74 g) and dimethylamine (3.1 ml).

The corresponding hydrochloride salt was obtained. M.p. 208°-210°.

2g
2-Dimethylaminomethyl-6-methyl-4(E)-(2-(3-ethoxy-3-oxo-2-ethyl-1-propenyl)phenyl)-1,4-dihydro-3,5-pyridine dicarboxylic acid diethyl ester (1.5 g) from Intermediate 5c (3 g) and diethylamine (3.1 ml).

The corresponding hydrochloride salt was obtained. M.p. 185°-187°.

2h
2-Dimethylaminomethyl-6-methyl-4(E)-(2-(3-ethoxy-3-oxo-2-propyl-1propenyl)phenyl)-1,4-dihydro-3,5-pyridinedicarboxylic acid diethyl ester hydrochloride. M.p. 118°-120°.

From Intermediate 5d (2.7 g) and dimethylamine (2.8 ml)

2i
2-Dimethylaminomethyl-6-methyl-4(E)-2(2-(3-propoxy-3-oxo-2-methyl-1-propenyl)phenyl)-1,4-dihydro-3,5-pyridinedicarboxylic acid diethyl ester hydrochloride M.p. 198°-199°. T.l.c. Rf 0.50

From Intermediate 7a (2.6 g) and dimethylamine (2.7 ml).

2j
2-Propylaminomethyl-6-methyl-4(E)-(2-(3,1,1-dimethylethoxy)-3-oxo-1-propenyl)phenyl)-1,4-dihydro-3,5-pyridinedicarboxylic acid diethyl ester (2.7 g). M.p. 70°-75°. T.l.c. Rf 0.34

From Intermediate 3 (4.55 g) and propylamine (5.1 ml). The corresponding hydrochloride salt was obtained by treating a solution of the free base (2.6 g) in acetone (50 ml) with 0.2N HCl (26 ml). The mixture was dried in vacuo and treated with diethyl ether to give the hydrochloride. M.p. 182°-184°. T.l.c. Rf 0.33.

2k
2-Pyrrolidinomethyl-6-methyl-4(E)-(2-(3-(1,1-dimethylethoxy)-3-oxo-1-propenyl)phenyl)-1,4-dihydro-3,5-pyridinedicarboxylic acid diethyl ester hydrochloride (1.2 g) m.p. 211°-213°

T.l.c. (Ethyl acetate/methanol 1:1) Rf 0.44
From Intermediate 3 (4.55 g) and pyrrolidine (4.15 ml).

2l
2-Piperazinomethyl-6-methyl-4(E)-(2-3(-1,1-dimethylethoxy-3-oxo-1-propenyl)phenyl)-1,4-dihydro-3,5-pyridinedicarboxylic acid diethyl ester dihydrochloride (3.6 g) m.p. 195°-200°

T.l.c. (Ethyl acetate/cyclohexane/methanol/20% NH2OH, 7:3:2:0.3) Rf 0.34.
From Intermediate 3 (6.8 g) and piperazine (0.75 g)

2m
2-Methylaminomethyl-6-methyl-4(E)-(2-(3-octyloxy-3-oxo-1-propenyl)phenyl)-1,4-dihydro-3,5-pyridinedicarboxylic acid diethyl ester hydrochloride (0.75 g) m.p. 200°-202° C.

T.l.c. as example 21 Rf 0.43 from methylamine (3.1 ml) and (E)-4-(2-(3-Octyloxy-3-oxo-1-propenyl)-phenyl)-1,4-dihydro-2,6-dimethyl-3,5-pyridinedicarboxylic acid diethyl ester (5.4 g).

2n
2-Methylaminomethyl-6-methyl-4(E)-(2-(3-cyclohexyloxy-3-oxo-1-propenyl)phenyl)-1,4-dihydro-3,5-pyridinedicarboxylic acid diethyl ester hydrochloride (0.40 g)

m.p. 210-211.
T.l.c. (Ethyl acetate/cyclohexane/methanol/20% NH4OH 7:3:2:0.2) Rf 0.18
From methylamine (3.45 ml) and (E)-4-(2-(3-cyclohexyloxy-3-oxo-1-propenyl)phenyl)-1,4-dihydro-2,6-dimethyl-3,5-pyridine dicarboxylic acid diethyl ester (5.65 g).

2-Methylaminomethyl-6-methyl-4(E)-(2-(3-isopropyloxy-3-oxo-1-propenyl)phenyl)-1,4-dihydro-3,5-pyridinedicarboxylic acid diethyl ester hydrochloride (1.1 g)

m.p. 218°-220° C.
T.l.c. as per example 2n Rf 0.24. from methylamine (3.1 ml) and (E) 4-(2-(3-(1-methylethoxy)-3-oxo-1-propenyl)phenyl-1,4-dihydro-2,6-dimethyl-3,5-pyridine-dicarboxylic acid diethyl ester (4.66 g).

2p
2-(1-Morpholinomethyl)-6-methyl-4(E)-2-(3-(1,1-dimethylethoxy)-3-oxo-1-propenyl)phenyl)-1,4-dihydro-3,5-pyridinedicarboxylic acid diethyl ester hydrochloride (3.5 g) M.p. 210°-12° C.

T.l.c. (ethyl acetate/cyclohexane 7:3) Rf 0.23. From intermediate 3 (6.83 g) and morpholine (9.1 ml).

2q
2-Dimethylaminomethyl-6-methyl-4(E)-(2-(3-pentyloxy-3-oxo-2-methyl-1-propenyl)phenyl-1,4-dihydro-3,5-pyridine dicarboxylic acid, diethyl ester, hydrochloride (0.38 g) M.p. 155°-57° C.

T.l.c. (ethyl acetate/cyclohexane/MeOH 7:3:1) Rf 0.33. From Intermediate 7b (1.3 g) and dimethylamine (1.3 ml).

2r
-2-(1-Morpholinomethyl)-6-methyl-4(E)-(2-(3-ethoxy)-3-oxo-2-methyl-1-propenyl)phenyl)-1,4-dihydro-3,5-pyridine dicarboxylic acid, diethyl ester, hydrochloride (1.21 g)

M.p. 14° C.
T.l.c. (Ethyl acetate/CH2Cl2 1:1) Rf 0.45. From Intermediate 5a (3 g) and morpholine (4.4 ml).

2s
2-Methylaminomethyl-6-methyl-4(E)-(2-(3-pentyloxy-3-oxo-2-methyl-1-propenyl)phenyl)-1,4 dihydro-3,5-pyridine dicarboxylic acid, diethyl ester, hydrochloride (3 g) m.p. 185°-186° C.

T.l.c. (Ethyl acetate/cyclohexane/MeOH 7:3:2) Rf 0.25. From Intermediate 7b (1.4 g) and methylamine (1.0 ml)

2t
2-Methylaminomethyl-6-methyl-4(E)-(2-(3-propoxy-3-oxo-2-methyl-1-propenyl)phenyl)-1,4-dihydro-3,5-pyridine dicarboxylic acid, diethyl ester, hydrochloride (0.67 g) M.p. 206°-208° C.

T.l.c. (Ethyl acetate/cyclohexane/MeOH 7:3:2). Rf=0.21 From Intermediate (7a) (2.66 g) and methylamine (1.9 ml).

2u 2-Ethylaminomethyl-6-methyl-4(E) (2-(3-ethoxy-3-oxo-2-ethyl-1-propenyl)phenyl)1,4-dihydro-3,5-pyridinedicarboxylic acid diethyl ester hydrochloride (1.7 g)

M.p. 149°-153° C.
T.l.c. (Ethyl acetate/cyclohexane/MeOH/NH4OH 20%, 7:3:2:0.3). Rf. 0.6 From Intermediate (5c) (5.63 g) and ethylamine (5 ml).

2v
2-Methylaminomethyl-6-methyl-4(E)(2-(3-propoxy-3-oxo-2-ethyl-1-propenyl)phenyl)-1,4-dihydro-3,5-pyridinedicarboxylic acid diethyl ester hydrochloride (0.98 g) M.p. 189°-190° C.

T.l.c. (1,1,1,Trichloroethane/MeOH/NH4OH 20%, 8:1:0.5) Rf=0.45.
From methylamine (3.1 ml) and Intermediate 7c (5.0 g)

2w

2-Methylaminomethyl-6-methyl-4(E)-(2-(3-(1,1-dimethylethoxy)-3-oxo-2-ethyl-1-propenyl)phenyl)-1,4-dihydro-3,5-pyridine dicarboxylic acid diethyl ester hydrochloride (1.2 g) M.p. 198°–200°.

T.l.c. (ethyl acetate/cyclohexane/MeOH/NH₄OH 20% 7:3:2:0.3). Rf=0.61. From methylamine (3.1 ml) and Intermediate 5e (5.13 g).

2x

2-Methylaminomethyl-6-methyl-4(E)-(2-(3-pentyloxy-3-oxo-2-ethyl-1-propenyl)phenyl-1,4-dihydro-3,5-pyridine-dicarboxylic acid diethyl ester hydrochloride m.p. 190°–200°.

T.l.c. From Intermediate 7d (1.8 g) and methylamime (3.1 ml).

2y

2-Piperidinomethyl-6-methyl-4(E)-(2-(3-(1,1-dimethylethoxy)3-oxo-1-propenyl)phenyl)1,4-dihydro-3,5-pyridine-dicarboxylic acid diethyl ester hydrochloride (2.98 g) M.p. 218°–220°.

T.l.c. (Cyclohexane/Acetone/MeOH 7:2:1) Rf=0.42. From Intermediate 3 (6.8 g) and piperidine (10.3 ml).

EXAMPLE 3

2-Dimethylaminomethyl-6-methyl-4(E)(2-(3-(1,1-dimethylethoxy)-3-oxo-1-propenyl)phenyl)-1,4-dihydro-3,5-pyridine dicarboxylic acid diethyl ester (1)

2-dimethylaminomethyl-6-methyl-4-(2-bromophenyl)-1,4-dihydro-3,5-pyridine-dicarboxylic acid diethyl ester Pyridine-hydrobromide-perbromide (7.68 g) was added to a solution of Intermediate 1 (6.86 g) and pyridine (2.6 ml) in anhydrous methylene chloride (100 ml) at 0° in 10 minutes. The mixture was stirred at 0° for 40 minutes and added to a solution of dimethylamine (6.3 g) in methylene chloride (50 ml) at 0° in 20 minutes. The resulting mixture was stirred for 30 minutes, the solid was filtered off and the solvent evaporated. The residue was dissolved in ethyl acetate, washed with 0.1N sodium hydroxide and water. After evaporation of the ethyl acetate the residue was eluted on a silica gel column (Ethyl acetate/cyclohexane 3:7) to give the title compound (4 g). M.p. 142°–143°. T.l.c. Rf 0.36.

(ii)

2-Dimethylaminomethyl-6-methyl-4(E)(2-(3-(1,1-dimethylethoxy)-3-oxo-1-propenyl)phenyl)-1,4-dihydro-3,5-pyridine-dicarboxylic acid diethyl ester A mixture of the product from stage (i) (3.71 g), tert-butylacrylate (1.21 ml), tri-n-butylamine (3 ml), palladium acetate (0.0225 g), triphenylphosphine (0.05 g) and tetrahydrofuran (5 ml) was heated with stirring at 110° for 72 hrs. The mixture was cooled, filtered and concentrated under vacuum to give a brown oil, which was purified by column chromatography using silica gel and eluting with ethyl acetate/methanol 9:1 to give the title compound as a yellow solid (1.15 mg), m.p. 146°–148°. T.l.c. (ethyl acetate/methanol 9:1) Rf=0.38. The title compound with maleic acid gave the maleate salt, m.p. 154°–156°.

EXAMPLE 4

(a)

2-(2-(N,N-Dimethylamino)ethyl)-4(E)-(2-(3-(1,1-dimethylethoxy)-3-oxo-1-propenyl)phenyl)-6-methyl-1,4dihydro-3,5-pyridine-dicarboxylic acid diethyl ester A mixture of Intermediate 3 (4.6 g), 35% solution of dimethylamine (3 ml), 40% solution of formaldehyde (1.15 ml) and acetic acid (10 ml) was refluxed for 5 h. After cooling to room temperature, water (150 ml) was added and then 10% NaOH until pH 9 was obtained. The solid obtained was filtered, washed with water and eluted on a silica gel column (1,1,1-trichloroethane/MeOH 1:1) to give, after crystallization from diethyl ether/n-hexane, the title compound (0.9 g). M.p. 150°–151° T.l.c. (1,1,1-trichloroethane/MeOH, 1:1) Rf 0.21.

(b)

2-(2-(N-Morpholino)ethyl)-4(E)-(2-(3-(1,1-dimethylethoxy)-3-oxo-1-propenyl)phenyl)-6-methyl-1,4-dihydro-3,5-pyridine-dicarboxylic acid diethyl ester A mixture of Intermediate 3 (9.2 g), morpholine (4.35 ml), 40% solution of formaldehyde (3.8 ml) and acetic acid (20 ml) was refluxed for 2 hrs. After cooling, water (about 250 ml) was added and then 10% NaOH until pH9 was obtained. The aqueous mixture was extracted with ethyl acetate and the organic layer washed with brine. After evaporation of the solvent the residue was purified by column chromatography to give after crystallization from methanol the title compound (1.6 g) m.p. 170°–172°. T.l.c. Rf 0.5.

(c)

2-(2-(N,N-Dimethylamino)ethyl)-6-methyl-4(E)-(2-(3-ethoxy-3-oxo-2-methyl-1-propenyl)-phenyl)-1,4-dihydro-3,5-pyridine dicarboxylic acid diethyl ester A mixture of Intermediate 5(a) (10 g), 35% solution of dimethylamine (4.55 ml), 40% solution of formaldehyde (2.34 ml) and acetic acid (20 ml) was refluxed for 1 h. Evaporation of the acetic acid in vacuo gave a residue that was treated with ethyl acetate, washed with 10% NaOH and water. After evaporation of the solvent, the residue was purified by column chromatography on silica gel (ethyl acetate/methanol 7:3) to give the title compound (3 g). M.p. 109° C. T.l.c. (1,1,1-trichloroethane/methanol 1:1) Rf 0.46.

EXAMPLE 5

5a

2-Methylaminomethyl-6-methyl-4(E)-(2-(3-ethoxy-3-oxo-2-ethyl-1-propenyl)phenyl)-1,4-dihydro-3,5-pyridinecarboxylic acid diethyl ester Pyridine-hydrobromide-perbromide (3.2 g) was added slowly to a solution of Intermediate 5c (4 g) and pyridine (1.3 ml) in methylene chloride (100 ml) at 0° C. and the mixture was stirred at the same temperature for 30 minutes. The cold solution was then added dropwise to a solution of methylamine (5 g) in methylene chloride (30 ml) at −30° C. for 15 minutes. The mixture was then stirred for 1 h, during which time the temperature rose to 0° C., and then poured into an ice water mixture. The aqueous solution was made alkaline by the addition of 10% aqueous sodium hydroxide solution, extracted with methylene chloride and the organic phase dried (Na₂SO₄). Evaporation of the solvent gave an oil (4.5 g)

which was eluted on a silica gel column to yield the title compound (3 g) m.p. 78°-80°.

5b

2-Methylaminomethyl-6-methyl-4(E)-(2-(3-ethoxy-3-oxo-2-ethyl-1-propenyl)phenyl)-1,4-dihydro-3,5-pyridinedicarboxylic acid diethyl ester hydrochloride salt

The compound of Example 5a (2.7 g) was dissolved in acetone (25 ml) and treated with 1N hydrochloric acid (5.5 ml). The solution was evaporated to a small volume, then acetone added and the mixture stirred at 0° for 20 h. The white solid (2.7 g) was filtered off and recrystallised from ethyl acetate/methanol (8:2) to give the title compound (2 g) as white solid m.p. 210°-212°.

5c

2-Methylaminomethyl-6-methyl-4(E)-(2-(3-ethoxy-3-oxo-2-ethyl-1-propenyl)phenyl)-1,4-dihydro-3,5-pyridinedicarboxylic acid diethyl ester hydrobromide salt

A mixture of the compound of Example 5a (1 g) hydrogen bromide (48%) 5 ml in ethyl acetate (30 ml) and water (5 ml) in ethyl acetate (30 ml) and water (50 ml) was stirred for 10 minutes. The mixture was filtered to give the title compound (0.6 g) as a yellow solid. M.p. 231°-233°.

The following salts were prepared in a similar manner from the compound example 5a and the appropriate acid.

5d

2-Methylaminomethyl-6-methyl-4(E)-(2-(3-ethoxy-3-oxo-2-ethyl-1-propenyl)phenyl)-1,4-dihydro-3,5-pyridinedicarboxylic acid diethyl ester tosylate M.p. 160°

5e

2-Methylaminomethyl-6-methyl-4(E)-(2-(3-ethoxy-3-oxo-2-ethyl-1-propenyl)phenyl)-1,4-dihydro-3,5-pyridinedicarboxylic acid diethyl ester formate M.p. 184°-185°

EXAMPLE 6

2-(N-benzyl-N-methyl)aminomethyl-6-methyl-(E)-4-(2-(3-(1,1-dimethylethoxy)-3-oxo-1-propenyl)phenyl)-1,4-dihydro-3,5-pyridinedicarboxylic acid 3-ethyl ester, 5-methyl ester

A solution of Intermediate 13a (12 g) and 3-amino-4-(N benzyl-N-methylamino)-2-butenoic acid ethyl ester (7.5 g) in ethanol (100 ml) was heated at reflux for 22 hours. The solvent was evaporated and the crude oil was eluted on a silica gel column (Ethyl acetate/petrol ether, 7:3) to yield the title compound as a pale yellow oil (3.7 g).

T.l.c. (Petrol ether/ethyl acetate, 7:3), Rf=0.27.

EXAMPLE 7

2-Methylaminomethyl-6-methyl-(E)-4-(2-(3-1,1-dimethylethoxy)-3-oxo-1-propenyl)phenyl)-1,4-dihydro-3,5-pyridinedicarboxylic acid 3-ethyl ester, 5-methyl ester, hydrochloride

2,2,2-Trichloroethylchloroformate (1.0 ml) was added to a solution of Example 6 (3.6 g) in dry toluene (35 ml) and the mixture heated at 50° C. for 45 minutes. The solvent was evaporated and the residue (3 g) was dissolved in dimethylformamide (40 ml) and treated with formic acid (0.7 g). Zinc (1.2 g) was then added, at 0° C., and the mixture was stirred for 1 hour at room temperature. Evaporation of the solvent gave an oil which was eluted on a silica gel column (Cyclohexane/Ethyl acetate/methanol, 7:3:2) to yield a colourless oil (3.2 g), which was dissolved in ethyl acetate and washed twice with water. The solvent was evaporated and the solid recrystallised from ethyl ether to give a yellow solid, which when treated with hydrochloric acid in methanol gave the title compound as a yellow solid (0.6 g), m.p. 208°-210° C.

T.l.c. (Ethyl acetate/methanol, 1:1), Rf.=0.22

EXAMPLE 8

2-Dimethylaminomethyl-6-methyl-4(E)-(2-(3-1,1-dimethylethoxy)-3-oxo-1-propenyl)phenyl)-1,4-dihydro 3,5-pyridine dicarboxylic acid diethyl ester hydrochloride

To a solution of Intermediate 3 (10 g) in methylene chloride (120 ml) cooled at −20° C., were added pyridine (1.7 g) and pyridinium bromide perbromide (6.68 g). The temperature of the solution was allowed to rise at +4° C. in 1.5 hrs, then again cooled at −20° C. N,N-Dimethylamine (4.9 g) was then added and the temperature allowed to rise to +15° in 1 hr. The solution was poured onto ice/water (200 ml approx.) the organic layer was separated and concentrated under vacuum. The residue was dissolved in ethyl acetate (200 ml) and washed twice with 10% aqueous sodium hydroxide (2×50 ml) and water (2×200 ml). The aqueous phase was dried over $Na_2SO_4$ and concentrated under vacuum to give a red oil, which was taken up with ethyl acetate (25 ml) and treated with a 1.2M solution of hydrogen chloride in ethyl acetate (20 ml). The mixture was left standing at 0° C. for one day, filtered, and the yellow solid washed with ethyl acetate (5 ml) and dried under vacuum to give the title compound as a yellow solid (7.6 g), m.p. 190°-193° C. T.l.c. (Ethyl acetate/methanol, 8:2) Rf=0.43

EXAMPLE 9

2-Dimethylaminomethyl-6-methyl-4(E)-(2-(3-1,1-dimethylethoxy)-3-oxo-1-propenyl)phenyl)-1,4-dihydro, 3,5-pyridine dicarboxylic acid diethyl ester hydrochloride

Intermediate 10a (6.25 g) was added to a solution of Intermediate 13b (5 g) in isopropyl alcohol (50 ml), and the mixture was warmed at 40°-45° C. for 48 hours. The solvent was removed by evaporation under vacuum, obtaining an orange residue which was dissolved with methylene chloride (100 ml) and washed twice with diluted hydrochloric acid with water. The organic layer was concentrated under vacuum and the residue was eluted on silica gel column (ethyl acetate/methanol 9:1) to obtain the title compound as a yellow solid (0.9 g), m.p. 190°-193° C.

T.l.c. (Ethyl acetate/methanol, 8:2) Rf=0.43.

EXAMPLE 10

(a) (−) (S)-(E)-4-(2-(3-(1,1-dimethylethoxy)-3-oxo-1-propenyl)-phenyl)-2-dimethylaminomethyl-6-methyl-1,4-dihydro-3,5-pyridine dicarboxylic acid, diethylester hydrochloride

(−)-Dibenzoyl-L-tartaric acid monohydrate (8.0 g) was added to a solution of (E)-4-(2-(3-(1,1-dimethylethoxy)-3-oxo-1-propenyl)phenyl)-2-dimethylaminomethyl-6-methyl-1,4-dihydro-3,5-pyridinedicarboxylic acid, diethylester (Example 3) (10.6 g) in isopropanol (360 ml) and the mixture was warmed to room temperature and stirred for 20h. The yellow crystals were collected by filtration and purified three times by recrystallisation from isopropanol. The solid (1.50 g) was dissolved in dichloromethane (50 ml) and treated with sodium hydroxide 10% (40 ml). The organic layer was evaporated, the residue was dissolved in ethyl acetate (20 ml) and acidified with hydrochloric acid in ethyl acetate 1,2N (2 ml). The solid was filtered off and dried to give the title compound (0.63 g). m.p. 202°–203° C.

T.l.c. (ethyl acetate/methanol, 8:2) Rf=0.43 $\alpha_D^{20} -69.2$ (c=1.04 in ethanol 95%).

In a similar manner

(b) (+)

(R)-(E)-4-(2-(3-(1,1-dimethylethoxy)-3-oxo-1-propenyl)phenyl-2-dimethylaminomethyl-6-methyl-1,4-dihydro-3,5-pyridinecarboxylic acid, diethylester hydrochloride (0.65 g) T.l.c. (ethyl acetate/methanol, 8:2) Rf=0.43; $\alpha_D^{20} = +68.5$ (c=1.04 in EtOH 95%) from the compound of Example 3 (10.6 g) with (+) dibenzoyl-D-tartaric acid monohydrate (8.0 g), m.p. 203° C.

EXAMPLE 11

2-Dimethylaminomethyl-6-methyl-(E)-4-(2-(3-(1,1-dimethylethoxy)-3-oxo-1-propenyl)phenyl)-1-1,4-dihydro-3,5-pyridine-dicarboxylic acid diethyl ester To a solution of Intermediate 8 (2.3 g) in toluene (20 ml) was added triphenylphosphoranylidene acetic acid, 1,1-dimethylethyl ester (0.38 g) and the mixture was heated at reflux for 8 hours. More phosphorane was added (0.38 g) and the mixture was heated at reflux for 8 hours. The solvent was evaporated and the residue was purified by column chromatography (Dichloromethane/Methanol, 95:5) to give the title compound as a yellow solid (0.1 g) (from Petrol/ether, 8:2), m.p. 146°–148° C.

T.l.c. (Dichloromethane/Methanol, 95:5)=0.30
T.l.c. (Ethyl acetate/methanol, 9:1)=0.38

EXAMPLE 12

2-Dimethylaminomethyl-6-methyl-(E)-4-(2-(3-(1,1-dimethylethoxy)-3-oxo-1-propenyl)phenyl-1,4-dihydro-3,5-pyridinedicarboxylic acid diethyl ester, hydrochloride A suspension of Intermediate 9 (0.1 g) and potassium carbonate (1 g) in N,N-dimethylformamide (10 ml) was treated with small portions of tert-butyl bromide (2.74 g) under vigorous stirring at room temperature, in four hours. The mixture was stirred at room temperature for two hours then poured into water and extracted with ethyl acetate, washed thoroughly with water and dried over Na$_2$SO$_4$. Evaporation of the solvent gave an oil (0.07 g). A sample of the base was treated with HCl/MeOH in ethyl ether to give the title compound as a yellow solid, m.p. 190°–193° C.

T.l.c. (Ethyl acetate/Methanol, 8:2) Rf=0.43

EXAMPLE 13

(a)

2-Dimethylaminomethyl-6-methyl-4(E)-(2-(3-(1,1-dimethylethoxy)-3-oxo-propenyl)phenyl)-1,4-dihydro-3,5-pyridinedicarboxylic acid, 3-ethyl, 5-methyl ester A mixture of the Intermediate 13(a) (18.33 g) and Intermediate 10(a) (5.1 g) in isopropanol was boiled for 24 hrs. After evaporation of the solvent the residue was eluted on a silica gel column (Ethyl acetate/cyclohexane/MeOH 7:3:2). The dihydropyridine (3.5 g) isolated was purified by crystallisation from petrol ether to give the title compound as a yellow solid (2 g), m.p. 126°–128° C.

In a similar manner (b)

2-Dimethylaminomethyl-6-methyl-4(E)-(2-(3-(1,1-dimethylethoxy)-3-oxo-propenyl)phenyl)-1,4-dihydro-3,5-pyridinedicarboxylic acid-3-methyl-5-ethyl ester was obtained as a white solid m.p. 132°–133° (1.2 g) From the Intermediate 13b (15.7 g) and Intermediate 10b (4.2 g).

T.l.c. (ethyl acetate/cyclohexane/MeOH/NH$_4$OH 20%, 7:3:2:0.3) Rf.=0.7.

(c)

2-Dimethylaminomethyl-6-methyl-4(E)-(2-(3-ethoxy-3-oxo-2-ethyl-1-propenyl)phenyl)-1,4-dihydro-3,5-pyridine-dicarboxylic acid, 3-ethyl, 5-methyl ester (0.51 g) as a white solid m.p. 98°–99° C.

From the Intermediate 13c (3.9 g) and Intermediate (10a) (1.9 g)

T.l.c. (ethyl acetate/cyclohexane/MeOH/NH$_4$OH 20%, 7:3:2:0.3) Rf.=0.32.

EXAMPLE 14

(Z)-2-Dimethylaminomethyl-6-methyl-4-(2-(3-ethoxy-3-oxo-2-bromo-1-propenyl)phenyl)-1,4-dihydro-3,5-pyridine dicarboxylic acid diethyl ester, hydrochloride Pyridine hydrochloride-perbromide (1.7 g) was added slowly to a solution of Intermediate 12 (2.3 g) and pyridine (0.8 ml) in dry dichloromethane (50 ml), at 0°. The mixture was stirred at 0° for 30 minutes and then added dropwise to a solution of dimethylamine (2.2 ml) in dichloromethane (20 ml) at 0°. The resulting mixture was stirred at 0° for 2h, the solvent evaporated and the residue taken up with ethyl acetate and washed with 10% HCl, 10% MeOH and brine. Evaporation of the solvent gave an oil which was eluted on a silica gel column to give the title compound (1.4 g) (from petrol ether/diethyl ether, 8:2) after treatment with 0.1N HCl. M.p. 193°–195°. T.l.c. (methylene chloride/methanol, 9:1) Rf=0.42.

EXAMPLE 15

Pharmaceutical Compositions (a) TABLETS

| (I) | mg/tablet |
|---|---|
| Active ingredient | 1 |
| Polyvinylpyrrolidone (PVP) | 20 |
| Lactose B.P. | 127 |
| Magnesium stearate B.P. | 2 |
| Compression weight | 150 |

The drug is granulated by a solution of PVP in ethanol, blended with the excipients and compressed using punches to suit.

| (II) | mg/tablet |
| --- | --- |
| Active ingredient | 1 |
| Microcrystalline cellulose BPC | 40 |
| Lactose B.P. | 100 |
| Sodium carboxymethylcellulose | 8 |
| Magnesium stearate B.P. | 1 |
| Compression weight | 150 |

The drug is sieved through a suitable sieve, blended with the excipients and compressed using punches to suit.

Tablets of other strengths may be prepared by altering the compression weight and using punches to suit. The tablets may be film coated with suitable film forming materials, e.g. methyl cellulose, ethyl cellulose or hydroxypropylmethyl cellulose, using standard techniques. Alternatively the tablets may be sugar coated.

(b) SOFT GELATIN CAPSULES

|  | mg/capsule |
| --- | --- |
| Active ingredient | 1 |
| Polyethylene glycol (PEG) 400 | 199 |
| Fill weight | 200 |

The drug is dissolved in PEG 400 with stirring and the mix is filled into soft gelatin capsules using a suitable filling machine. Other doses may be prepared by altering the fill weight and if necessary changing the capsule size to accommodate the change in fill weight.

| Injection | amount/ampoule |
| --- | --- |
| *Active ingredient | 1.0 mg |
| Water for Injection | to 2.0 ml |

*amount expressed as free base.

The drug is dissolved in water for injection under stirring. The solution is sterilised by filtration and filled in glass ampoules under sterile conditions. Other doses may be prepared by altering the filling volume or the concentration of the active ingredient.

In the above pharmaceutical examples the active ingredient refers to one or more compounds of the general formula (I) but is preferably 2-dimethylaminomethyl-6-methyl-4-(2-(3-(1,1-dimethylethoxy)-3-oxo-1-propenyl)phenyl)-1,4-dihydro-3,5-pyridine-dicarboxylic acid diethyl ester and more especially the E isomer and S-enantiomers thereof.

What we claim is:

1. A compound of the formula (I):

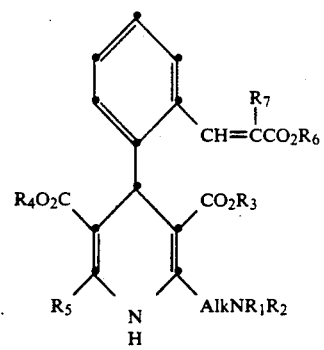

or a physiologically acceptable salt thereof, in which $R_1R_2N$ represents amino, methylamino, isopropylamino or dimethylamino, Alk represents a methylene chain, $R_3$ and $R_4$ represent methyl or ethyl, $R_5$ represents a methyl group, and $R_7$ represents a hydrogen atom and $R_6$ represents a tert butyl group.

2. 2-dimethylaminomethyl-6-methyl-4-(2-(3-(1,1-dimethyl-ethoxy)-3-oxo-1-propenyl)phenyl-1-4-dihydropyridine-3,5-dicarboxylic acid diethyl ester; or a physiologically acceptable salt thereof.

3. 2-methylaminomethyl-6-methyl-4-(2-(3-(1,1-dimethyl-ethoxy)-3-oxo-1-propenyl)phenyl)-1,4-dihydropyridine-3,5-dicarboxylic acid diethyl ester;
2-aminomethyl-6-methyl-4-(2-(3-(1,1-dimethylethoxy)-3-oxo-1-propenyl)phenyl)-1,4-dihydropyridine-3,5-dicarboxylic acid diethyl ester;
2-isopropylaminomethyl-6-methyl-4-(2-(3-(1,1-dimethyl-ethoxy)-3-oxo-1-propenyl)phenyl)-1,4-dihydro-pyridine-3,5-dicarboxylic acid diethyl ester
or a physiologically acceptable salt thereof.

4. A compound as claimed in any of claims 1, 2 or 3, wherein the compound is a trans isomer.

5. A compound as claimed in any of claims 2, 3, 4 or 1, wherein the compound is an S-enantiomer.

6. A pharmaceutical composition comprising a compound as claimed in claim 1 in association with a pharmaceutically acceptable carrier or diluent.

7. A composition as claimed in claim 6 in a form suitable for oral, sublingual, transdermal, parenteral or rectal administration, or for administration by inhalation or insufflation.

8. A composition as claimed in claim 7 for oral administration in the form of a tablet or capsule.

9. A composition as claimed in claim 8 containing a dose or 0.3 to 40 mg of active ingredient.

10. A method of treating cardiovascular disorders arising from transmembranal calcium ion influx comprising administering to a patient in need of such treatment an effective amount of a compound according to claim 1.

11. A method of treating cardiovascular disorders arising from transmembranal calcium ion influx comprising administering to a patient in need of such treatment an effective amount of a compound according to claim 2.

12. A method of treating cardiovascular disorders arising from transmembranal calcium ion influx comprising administering to a patient in need of such treatment an effective amount of a compound according to claim 3.

13. A method of treating cardiovascular disorders arising from transmembranal calcium ion influx comprising administering to a patient in need of such treatment an effective amount of a compound according to claim 4.

14. A method of treating cardiovascular disorders arising from transmembranal calcium ion influx comprising administering to a patient in need of such treatment an effective amount of a compound according to claim 5.

15. A method of treating cardiovascular disorders comprising administering to a patient in need of such treatment an effective amount of a compound according to claim 1, wherein the cardiovascular disorder is hypertension, angina pectoris, or myocardial ischemia.

16. A method of treating cardiovascular disorders comprising administering to a patient in need of such treatment an effective amount of a compound according to claim 2, wherein the cardiovascular disorder is hypertension, angina pectoris, or myocardial ischemia.

17. A method of treating cardiovascular disorders comprising administering to a patient in need of such treatment an effective amount of a compound according to claim 3, wherein the cardiovascular disorder is hypertension, angina pectoris, or myocardial ischemia.

18. A method of treating cardiovascular disorders comprising administering to a patient in need of such treatment an effective amount of a compound according to claim 4, wherein the cardiovascular disorder is hypertension, angina pectoris, or myocardial ischemia.

19. A method of treating cardiovascular disorders comprising administering to a patient in need of such treatment an effective amount of a compound according to claim 5, wherein the cardiovascular disorder is hypertension, angina pectoris, or myocardial ischemia.

* * * * *